(12) United States Patent
Goshen

(10) Patent No.: US 10,282,820 B2
(45) Date of Patent: May 7, 2019

(54) STRUCTURE PROPAGATION RESTORATION FOR SPECTRAL CT

(71) Applicant: KONINKLIJKE PHILIPS N.V., Eindhoven (NL)

(72) Inventor: Liran Goshen, Pardes-Hanna (IL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 133 days.

(21) Appl. No.: 14/766,999

(22) PCT Filed: Feb. 11, 2014

(86) PCT No.: PCT/IB2014/058895
§ 371 (c)(1),
(2) Date: Aug. 11, 2015

(87) PCT Pub. No.: WO2014/128595
PCT Pub. Date: Aug. 28, 2014

(65) Prior Publication Data
US 2015/0379694 A1  Dec. 31, 2015

Related U.S. Application Data

(60) Provisional application No. 61/767,300, filed on Feb. 21, 2013.

(51) Int. Cl.
*G06T 5/00* (2006.01)
*G06K 9/52* (2006.01)
(Continued)

(52) U.S. Cl.
CPC .............. *G06T 5/002* (2013.01); *A61B 6/032* (2013.01); *A61B 6/482* (2013.01); *A61B 6/5205* (2013.01);
(Continued)

(58) Field of Classification Search
CPC ........... G06T 5/002; G06T 2207/10072; G06T 2207/30004; G06T 11/005;
(Continued)

(56) References Cited

U.S. PATENT DOCUMENTS 5,825,846 A   10/1998  Aach et al.
8,938,110 B2   1/2015  Goshen et al.
(Continued)

FOREIGN PATENT DOCUMENTS

WO       2011064683 A2      6/2011
WO   WO 2011064683 A2 *    6/2011   ............. G06T 5/002
(Continued)

OTHER PUBLICATIONS

Alvarez, R. E., et al.; Energy-selective Reconstructions in X-ray Computerized Tomography; 1976; Phys. Med. Biol.; 21(5)733-744.
(Continued)

*Primary Examiner* — Kim Y Vu
*Assistant Examiner* — Michael J Vanchy, Jr.

(57) ABSTRACT

A method includes obtaining at least one of projection data from a spectral scan or image data generated from the projection data, selecting a local reference dataset from the at least one of the projection data or the image data, determining a noise pattern for the selected reference dataset, estimating underlying local structure from the reference dataset based on the noise pattern, and restoring at least one of the projection data or the image data based on the estimated underlying local structure.

20 Claims, 3 Drawing Sheets

(51) Int. Cl.
*G06T 7/00* (2017.01)
*G06K 9/46* (2006.01)
*A61B 6/03* (2006.01)
*A61B 6/00* (2006.01)
*G06T 11/00* (2006.01)

(52) U.S. Cl.
CPC .............. *A61B 6/5258* (2013.01); *G06K 9/46* (2013.01); *G06K 9/468* (2013.01); *G06K 9/52* (2013.01); *G06T 7/0014* (2013.01); *G06T 11/005* (2013.01); *G06K 2009/4666* (2013.01); *G06T 2207/10081* (2013.01); *G06T 2211/408* (2013.01)

(58) Field of Classification Search
CPC . G06T 2207/10081; G06T 2207/20028; G06T 2211/408; G06T 7/0014; A61B 6/032; A61B 6/482; A61B 6/5258; A61B 6/5205; G06K 9/46; G06K 9/468; G06K 9/52
See application file for complete search history.

(56) References Cited

U.S. PATENT DOCUMENTS

| | | | |
|---|---|---|---|
| 2005/0105693 A1 | 5/2005 | Zhao et al. | |
| 2005/0111751 A1* | 5/2005 | Avinash | G06T 5/20 382/275 |
| 2009/0052612 A1* | 2/2009 | Wu | A61B 6/032 378/5 |
| 2010/0061656 A1 | 3/2010 | Wiemker | |
| 2010/0166277 A1 | 7/2010 | Raupach | |
| 2010/0220912 A1 | 9/2010 | Bruder et al. | |
| 2014/0133729 A1 | 5/2014 | Goshen | |

FOREIGN PATENT DOCUMENTS

| | | | | |
|---|---|---|---|---|
| WO | WO 2011073863 A1 * | 6/2011 | ............ | A61B 6/032 |
| WO | 2013011418 A2 | 1/2013 | | |

OTHER PUBLICATIONS

Comaniciu, D., et al.; Mean Shift: A Robust Approach toward Feature Space Analysis; 2002; IEEE PAMI; pp. 1-37.

Leng, S., et al.; Noise reduction in spectral CT: Reducing dose and breaking the trade-off between image noise and energy bin selection; 2011; Med. Phys.; 38(9)4946-4957.

Perona, P., et al.; Scale-Space and Edge Detection Using Anisotropic Diffusion; 1990; IEEE PAMI; 12(7)629-639.

Rudin, L. I., et al.; Nonlinear total variation based noise removal algorithms; 1992; Physica D; 60:259-268.

Tomasi, C., et al.; Bilateral Filtering for Gray and Color Images; 1998; IEEE International Conf. on Computer Vision; pp. 1-8.

Wunderlich, A., et al.; Image Covariance and Lesion Detectability in Direct Fan-Beam X-Ray Computed Tomography; 2008; Phys. Med. Biol.; 53(10)2471-2493.

* cited by examiner

STRUCTURE PROPAGATION RESTORATION FOR SPECTRAL CT

CROSS REFERENCE TO RELATED APPLICATIONS

This application is a national filing of PCT application Serial No. PCT/IB2014/058895, filed Feb. 11, 2014, published as WO 2014/128595 A1 on Aug. 28, 2014, which claims the benefit of U.S. provisional application Ser. No. 61/767,300 filed Feb. 21, 2013, which is incorporated herein by reference.

The following generally relates to spectral projection data and/or spectral image data processing and more particularly to structure propagation restoration for spectral projection data and/or spectral image data, and is described with particular application to computed tomography (CT). However, the following is also amenable to other imaging modalities.

Spectral (or multi-energy) CT has utilized two attenuation values (e.g., with dual energy CT) acquired simultaneously at two different photon energies to solve the photoelectric and Compton contribution that consists of the mass attenuation coefficients of a scanned material and then identify an unknown material by its value of photoelectric and Compton contribution. This approach is well-suited with materials such as iodine that have a k-edge energy close to a mean value of a diagnostic energy range. Because any two linearly independent sums of two basis functions span the entire attenuation coefficient space, any material can be represented by a linear combination of two other materials, generally referred to as basis materials, such as water and iodine.

The basis material images provide new applications such as monochromatic image, material cancellation image, effective atomic number image and electron density image. With the recent technical advances there are several approaches to perform dual energy CT acquisition such as dual-source, fast kVp switching, and dual-layer detector configuration. In addition, quantitative imaging is one of the current major trends in the medical imaging community. Spectral CT supports this trend, as the additional spectral information improves the quantitative information that can be measured about the scanned object and its material composition.

Dual energy material decomposition is a mathematical scheme to extract beam-hardening free line integrals representing two basis materials, i.e. the photoelectric absorption and Compton scattering within the scanned object. However, spectral CT suffers from an inherently noise challenge, especially in scenarios in which a material decomposition is conducted. As the material decomposition is an ill-posed problem, the decomposition amplifies the noise significantly, where the obtained noise is highly anti-correlated between the materials. Unfortunately, if images are directly reconstructed from the material line integrals, the images are very noisy. As a result, the obtained image quality is low, which may reduce the clinical value of the image.

Aspects described herein address the above-referenced problems and others.

The following describes an approach that improves spectral CT image quality using a restoration algorithm that removes noise and/or artifacts from an imaging study (i.e., the projection data and/or the image data), while preserving the underlying object structure and spectral information. The algorithm can be applied in the projection domain, the image domain, or in both the projection and the image domains. Generally, a reference dataset, i.e., images or sinograms, is derived from the projection or image data of a spectral scan and used, in connection with a determined noise pattern, to estimate underlying local object structures, which are also utilized as additional constraints. The estimate and, optionally, the additional constraints provide a robust and quality restoration that removes noise and/or artifacts.

In one aspect, a method includes obtaining at least one of projection data from a spectral scan or image data generated from the projection data, selecting a local reference dataset from the at least one of the projection data or the image data, determining a noise pattern for the selected reference dataset, estimating underlying local structure from the reference dataset based on the noise pattern, and restoring at least one of the projection data or the image data based on the estimated underlying local structure.

In another aspect, a projection data and/or image data processor includes a memory that stores a structure propagation algorithm and a processor that executes the structure propagation algorithm in connection with at least one of projection data or image data from a spectral scan to remove at least one of noise or artifacts from the at least one of projection data or the image data, while preserving underlying object structure and spectral information.

In another aspect, a computer readable storage medium is encoded with computer readable instructions. The computer readable instructions, when executed by a processor, causes the processor to: obtain at least one of projection data from a spectral scan or image data generated based on the projection data, select a local reference dataset from the at least one of the projection data or the image data, determine a noise pattern for the selected reference dataset, estimate underlying local structure from the reference dataset based on the noise pattern, and restore at least one of projection data or image data based on the estimated underlying local structure.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with a projection data and/or image data processor employing a structure propagation restoration algorithm.

FIG. 2 schematically illustrates example models of the structure propagation restoration algorithm.

The following describes an approach that improves spectral CT image quality using a restoration algorithm that removes noise and/or artifacts from projection data and/or image data of a spectral imaging study, while preserving underlying object structure and spectral information.

Figure 1:
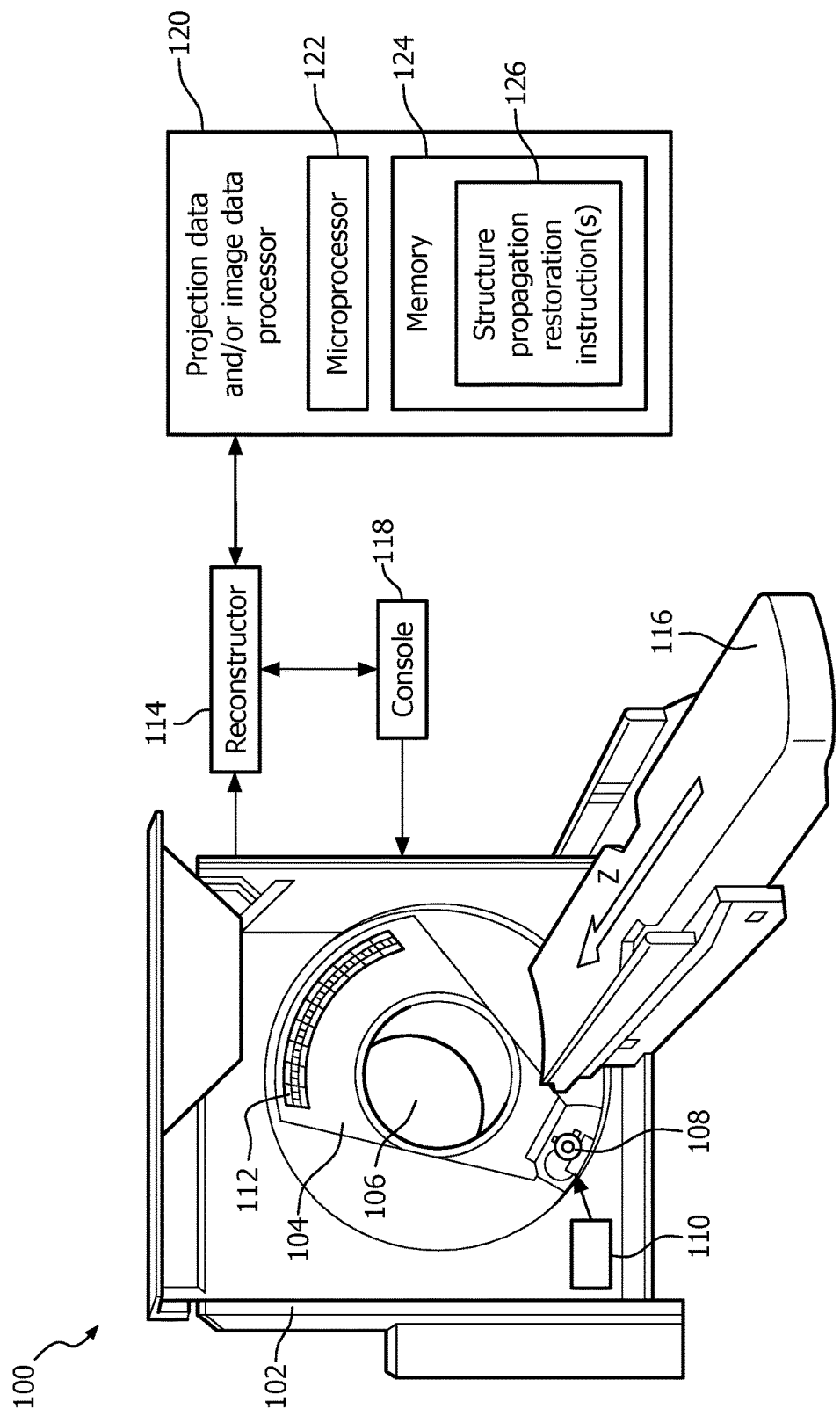

Initially referring to FIG. 1, a spectral imaging system 100 such as a spectral computed tomography (CT) scanner is illustrated. The illustrated spectral imaging system 100 utilizes kVp switching, as discussed in greater detail below, to produce spectral projection data. The spectral imaging system 100 includes a generally stationary gantry 102 and a rotating gantry 104, which is rotatably supported by the stationary gantry 102 and rotates around an examination region 106 about a z-axis.

A radiation source 108, such as an x-ray tube, is rotatably supported by the rotating gantry 104, rotates with the rotating gantry 104, and emits radiation that traverses the examination region 106. A radiation source voltage controller 110 controls a mean or peak emission voltage of the radiation source 108. In one instance, this includes switching the emission voltage between two or more emission voltages (e.g., 80 keV and 140 keV, 100 keV and 120 keV, etc.) between views of a scan, within a view of a scan, and/or otherwise.

A detector array 112 subtends an angular arc opposite the examination region 106 relative to the radiation source 108. The detector array 112 detects radiation that traverses the examination region 106 and generates projection data indicative thereof. Where the scan is a multiple energy scan and the radiation source voltage is switched between at least two emission voltages for the scan, the detector array 112 generates projection data (also referred herein as a sinogram) for each of the radiation source voltages.

Again, the illustrated spectral imaging system 100 utilizes kVp switching. In a variation, the spectral imaging system 100 includes at least two radiation sources 108 that emit radiation at two different emission voltages to produce spectral projection data and/or the detector array 112 includes an energy-resolving detector that produces spectral projection data. In still another variation, the spectral imaging system 100 includes a combination of the above and/or other approach to produce spectral projection data.

A reconstructor 114 reconstructs the spectral projection data, generating volumetric image data indicative of a scanned portion of a subject or object located in the examination region 106. This includes reconstructing spectral image data at one or more emission voltages and/or conventional (non-spectral) image data over the entire emission spectrum. A couch or subject support 116 supports a subject or object in the examination region 106.

An operator console 118 includes a human readable output device such as a monitor and an input device such as a keyboard, mouse, etc. Software resident on the console 118 allows the operator to interact with and/or operate the spectral imaging system 100 via a graphical user interface (GUI) or otherwise. This may include selecting a multi-energy spectral imaging protocol in which the emission voltage is switched between two or more emission voltages.

A projection data and/or image data processor 120 includes at least one microprocessor 122 that executes at least one computer readable instruction stored in computer readable storage medium, such as physical memory 124 or other non-transitory storage medium. The microprocessor 122 may also executes one or more computer readable instructions carried by a carrier wave, a signal or other transitory medium. The projection data and/or image data processor 120 can be part of the console 118 and/or other computing system.

The at least one computer readable instruction includes a structure propagation restoration instruction(s) 126, which can be applied to spectral projection data (or the spectral domain) and/or reconstructed image data (or the image domain). Where the structure propagation restoration instruction(s) 126 is applied to both, it is first applied to spectral projection data, generating restored projection data, which is then reconstructed to generate image data, and then the structure propagation restoration instruction(s) 126 is applied to the reconstructed image data.

As described in greater detail below, executing the structure propagation restoration instruction(s) 126 includes selecting a reference projection and/or image dataset from input projection data and/or image data, determining a noise model therefrom, estimating underlying local object structure from the reference dataset based on the noise model, and propagating the estimated underlying local object structure through the input projection data and/or image data, restoring the projection and/image data.

Optionally, the estimated underlying local object structure can be used as a constraint on the restoration. Furthermore, some of the removed texture and/or noise can be added back. It is to be appreciated that the structure propagation restoration instruction(s) 126 improves image quality of the spectral data through removing noise and/or artifacts, while preserving the underlying object structure and spectral information.

The restored projection data and/or the restored image data can be further processed, displayed via a display monitor, filmed, archived in a data repository (e.g., a picture archiving and communication system or PACS, an electronic medical record or EMR, a radiology information system or RIS, a hospital information system or HIS, etc.), and/or otherwise utilized.

Figure 2:
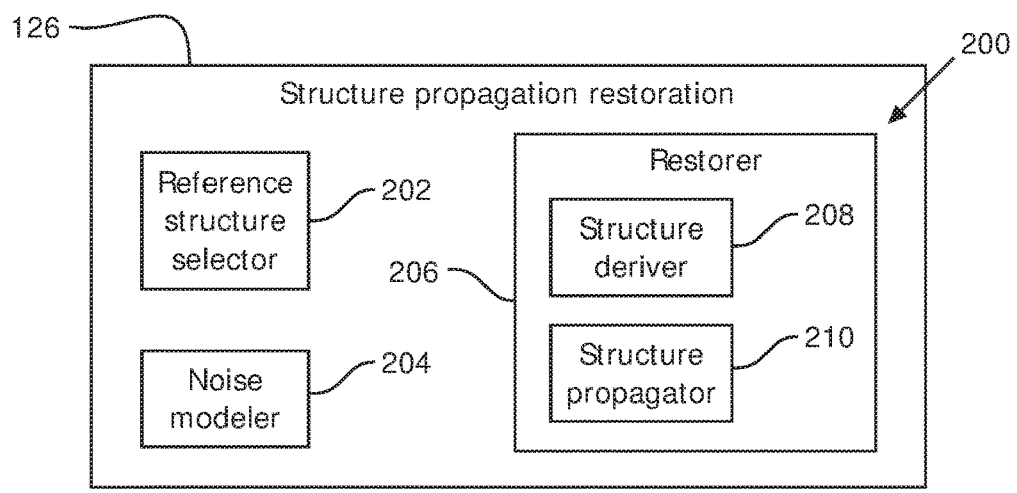

FIG. 2 schematically illustrates example modules 200 of the structure propagation restoration instruction(s) 126.

A reference structure selector 202 selects a local reference dataset from input projection and/or image data, which can be generated by the imaging system 100 (FIG. 1) and/or other system. The criterion for the reference dataset selection includes reference data in which underlying local object structures can be derived or estimated from. Examples of suitable references image data include, but are not limited to: a specific monochromatic image (e.g., 70 keV) since the noise is anti-correlated between the materials and there is a specific monochromatic image in which the contrast to noise ratio (CNR) is optimal; a non-spectral (or conventional) CT image, a combined spectral/non-spectral image such as a non-spectral CT image based on all of the energies or the whole spectrum, which may allow for extracting structure more accurately; a low energy image and/or a high energy image based only on partial spectrum, and/or other reference image.

Examples of suitable references projection data include, but are not limited to: a specific monochromatic sinogram (e.g., 70 keV) since the noise is anti-correlated between the materials and a non-spectral (or conventional) CT sinogram, a combined spectral/non-spectral sinogram such as a non-spectral CT sinogram based on all of the energies or the whole spectrum without material decomposition; a low energy sinogram and/or a high energy sinogram based only on partial spectrum without material decomposition, and/or other reference projection data.

In one instance, a global approach is utilized to select the reference data. For this approach, a single reference dataset can be selected for the entire received projection and/or image data. The selection can be based on one or more of the following criteria: a minimum total variation; a minimum entropy; a minimum median over a local standard deviation of the image/sinogram; a minimum average of local noise estimate; a CNR image based on input of two ROI's, etc. An example for total variation selection criterion among monochromatic images is shown in EQUATION 1:

$$\hat{e} = \underset{e}{\operatorname{argmin}} \int\int_{i,j} |\nabla R_{i,j}^e|\, di\, dj,\qquad \text{EQUATION 1}$$

where e is the monochromatic energy and $R_{i,j}^e$ is the i,j pixel in the reference image R.

In another instance, a local approach is utilized to select the reference data. For this approach, for each pixel, an optimal reference dataset patch (or sub-set of projection and/or image data) is selected. The patch can be selected around a location of the pixel from one of the potential reference datasets. This approach utilizes the fact that different regions in the input projection and/or image data might have a different optimal reference dataset for local structure derivation.

A noise modeler 204 models a noise pattern of the selected reference dataset. Examples of suitable modeling approaches includes, but is not limited to, a Monte Carlo estimate, analytics, direct extraction and/or other approaches. The obtained noise pattern or model is utilized to estimate the local structures reference dataset. An example analytical approach is described in Wunderlich, "Image Covariance and Lesion Detectability in Direct Fan-Beam X-Ray Computed Tomography", Phys. Med. Biol. 53 (2008), 2472-2493.

Examples of direct extraction approaches are described in application Ser. No. 61/264,340, filed Nov. 25, 2009, and entitled "ENHANCED IMAGE DATA/DOSE REDUCTION," which is incorporated herein by reference in its entirety, and application Ser. No. 61/286,477, filed Dec. 15, 2009, and entitled "ENHANCED IMAGE DATA/DOSE REDUCTION," which is incorporated herein by reference in its entirety. Other approaches are also contemplated herein.

A restorer 206 restores the projection data and/or image data. The illustrated restorer 206 includes a structure deriver 208 and a structure propagator 210.

The structure deriver 208 estimates the underlying local structure from the reference dataset. The estimate may improve the local CNR of the reference dataset, which facilitates estimating the dataset structures and enables a very accurate structure estimate. The structure deriver 208 utilizes the noise model generated by the noise modeler 204 as a guide, which facilitates differentiation between the noise and the underlying object structures.

For the estimate, the structure deriver 208 may utilize various algorithms such as bilateral filtering, diffusion filtering, total variation de-noising, mean shifting, etc. By way of non-limiting example, the following describes an approach using a bilateral algorithm to estimate the local structures. This example includes an optional spike noise suppression.

For each voxel $R_{i,j,k}$ in the reference dataset, R, the structure deriver 208 performs the following:
1. Extract a sub-volume of n voxels around voxel $R_{i,j,k}$;
2. Calculate a kernel $w_{i',j',k'}^{range}$ based on EQUATION 2:

$$w_{i',j',k'}^{range} = \exp\left(-\frac{(R_{i,j,k} - R_{i+i',j+j',k+k'})^2}{2(\alpha\sigma_{i,j,k}^{Noise})^2}\right),\qquad \text{EQUATION 2}$$

where α is a parameter that controls a aggressiveness of the weights and $\sigma_{i,j,k}^{Noise}$ is a local noise level estimate of $R_{i,j,k}$ estimated in the above-discussed noise modeling;

3. Multiply a local kernel by a spatial kernel: $w_{i',j',k'} = (w^{spatial}_{i',j',k'*w})(w_{i',j',k'}^{range})$, where a three dimensional (3D) spatial Gaussian kernel with standard deviation can be determined based on EQUATION 3:

$$w_{i',j',k'}^{spatial} = \sqrt{\exp\left(-\frac{((i'dx)^2 + (j'dx)^2 + (k'dz)^2)}{2\sigma_{spatial}^2}\right)},\qquad \text{EQUATION 3}$$

where dx is a size of a pixel (e.g., in millimeters or mm), dz is a slice width (e.g., in mm), and $\sigma_{spatial}$ is a parameter that controls an aggressiveness of the weights;
4. Normalize $w_{i',j',k'}$ to have sum equal to one;
5. Apply spike noise suppression as follows: if a central weight $w_{i',j',k'} > w_{Threshold}$ and $\alpha < \alpha_{max}$, then $\alpha = \alpha * \alpha_{ult}$ and return to step 2; and
6. Estimate the object structure based on EQUATION 4:

$$\hat{R}_{i,j,k}^{NR} = \frac{\sum_{i'=-n}^{n}\sum_{j'=-n}^{n}\sum_{k'=-n}^{n} R_{i+i',j+j',k+k'} w_{i',j',k'}}{\sum_{i'=-n}^{n}\sum_{j'=-n}^{n}\sum_{k'=-n}^{n} w_{i',j',k'}}.\qquad \text{EQUATION 4}$$

The structure propagator 210 propagates the estimated structure to the input projection data and/or image data and, optionally, the estimate is utilized as additional constraints of the restoration. Some of the removed texture and/or noise can be added back during restoration. This may facilitate controlling final image appearance.

For this, the structure propagator 210 derives the local structures according to the output of the structure deriver 208, and the noise level is defined according to the output of the noise modeler 204. A strength of this approach is that it utilizes a very well defined local structure with improved local CNR. Since the processing is done over the projection data and/or image data, the intensity values of the projection data and/or image data are preserved very accurately.

By way of non-limiting example, in one instance, the structure propagator 210 performs N iterations of the following for each voxel $V_{i,j,k}$ in the projection data and/or image data:
1. Extract a sub-volume of n voxels around the voxel $V_{i,j,k}$;
2. Calculate a local kernel $w_{i',j',k'}^{range}$ based on EQUATION 4:

$$w_{i',j',k'}^{range} = \exp\left(-\frac{(\hat{R}_{i,j,k}^{NR} - \hat{R}_{i+i',j+j',k+k'}^{NR})^2}{2(\beta\sigma_{i,j,k}^{Noise})^2}\right),\qquad \text{EQUATION 4}$$

where β is an input parameter;
3. Multiply the local kernel by $w_{i',j',k'} = w_{i',j',k'} = (w^{spatial}_{i',j',k'*w})(w_{i',j',k'}^{range})$;
4. Normalize $w_{i',j',k'}$ to have sum equal to one; and
5. Process the projection data and/image data as shown in EQUATION 5:

$$\hat{V}_{i,j,k}^{Iter} = \frac{\sum_{i'=-n}^{n}\sum_{j'=-n}^{n}\sum_{k'=-n}^{n} V_{i+i',j+j',k+k'}^{Iter-1} w_{i',j',k'}}{\sum_{i'=-n}^{n}\sum_{j'=-n}^{n}\sum_{k'=-n}^{n} w_{i',j',k'}} \quad \text{EQUATION 5}$$

where $\hat{V}_{i,j,k}^{Iter=0} = V_{i,j,k}$ input target dataset and Iter is an index of a current iteration.

In step 5, some of the image texture and/or noise can be added back to the target dataset to control its final appearance. There are two optional sources for the texture and/or noise: the reference projection data and/or image data or the target projection data and/or image data.

The final restoration is obtained as shown in EQUATION 6 or EQUATION 7:

$$V^{Final} = \hat{V}^{Iter=N}\delta + (\hat{V}^{Iter=0} - \hat{V}^{Iter=N})(1-\delta) \quad \text{EQUATION 6:}$$

Or $$V^{Final} = \hat{V}^{Iter=N}\delta + (R - \hat{R}^{NR})(1-\delta) \quad \text{EQUATION 7:}$$

where δ is an input parameter.

FIGS. 3-8 show example results of the restoration in connection with images generated without the restoration.

Figure 3:
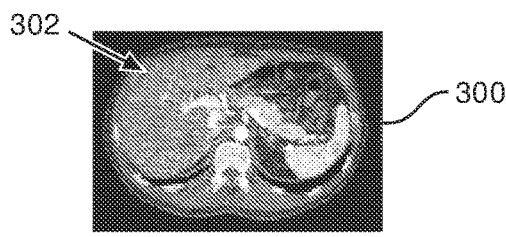
FIG. 3 illustrates a prior art image reconstructed from first projection data.
Figure 4:
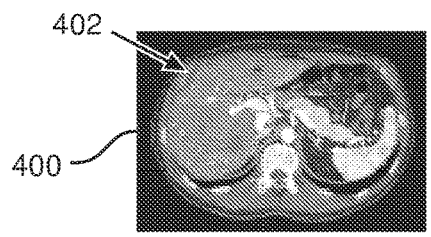
FIG. 4 illustrates a restored image, using the structure propagation restoration approach described herein in connection with the first projection data.

For a first set of projection data and/or image data, FIG. 3 represents a prior art image 300 where the structure propagation restoration instruction(s) 126 was not utilized, and FIG. 4 represents an image 400 where the structure propagation restoration instruction(s) 126 was utilized. As shown, a region 402 is less noisey than a corresponding region 302, without visible loss of structure in the image 400.

Figure 5:
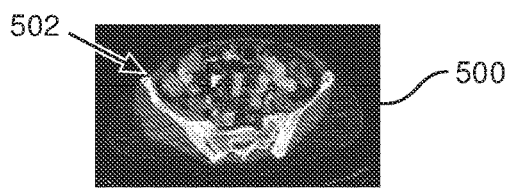
FIG. 5 illustrates a prior art image reconstructed from second projection data.
Figure 6:
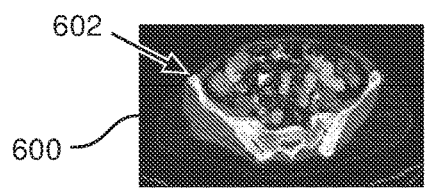
FIG. 6 illustrates a restored image, using the structure propagation restoration approach described herein in connection with the second projection data.

For a second set of projection data and/or image data, FIG. 5 represents a prior art image 500 where the structure propagation restoration instruction(s) 126 was not utilized, and FIG. 6 represents an image 600 where the structure propagation restoration instruction(s) 126 was utilized. As shown, a region 602 is less noisey than a corresponding region 502, without visible loss of structure in the image 600.

Figure 7:
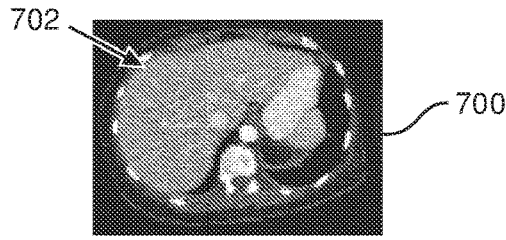
FIG. 7 illustrates a prior art image reconstructed from third projection data.
Figure 8:
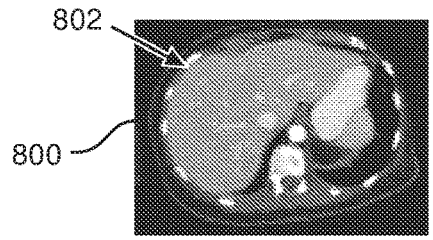
FIG. 8 illustrates a restored image, using the structure propagation restoration approach described herein in connection with the third projection data.

For a third set of projection data and/or image data, FIG. 7 represents a prior art image 700 where the structure propagation restoration instruction(s) 126 was not utilized, and FIG. 8 represents an image 800 where the structure propagation restoration instruction(s) 126 was utilized. As shown, a region 802 is less noisey than a corresponding region 702, without visible loss of structure in the image 800.

Figure 9:
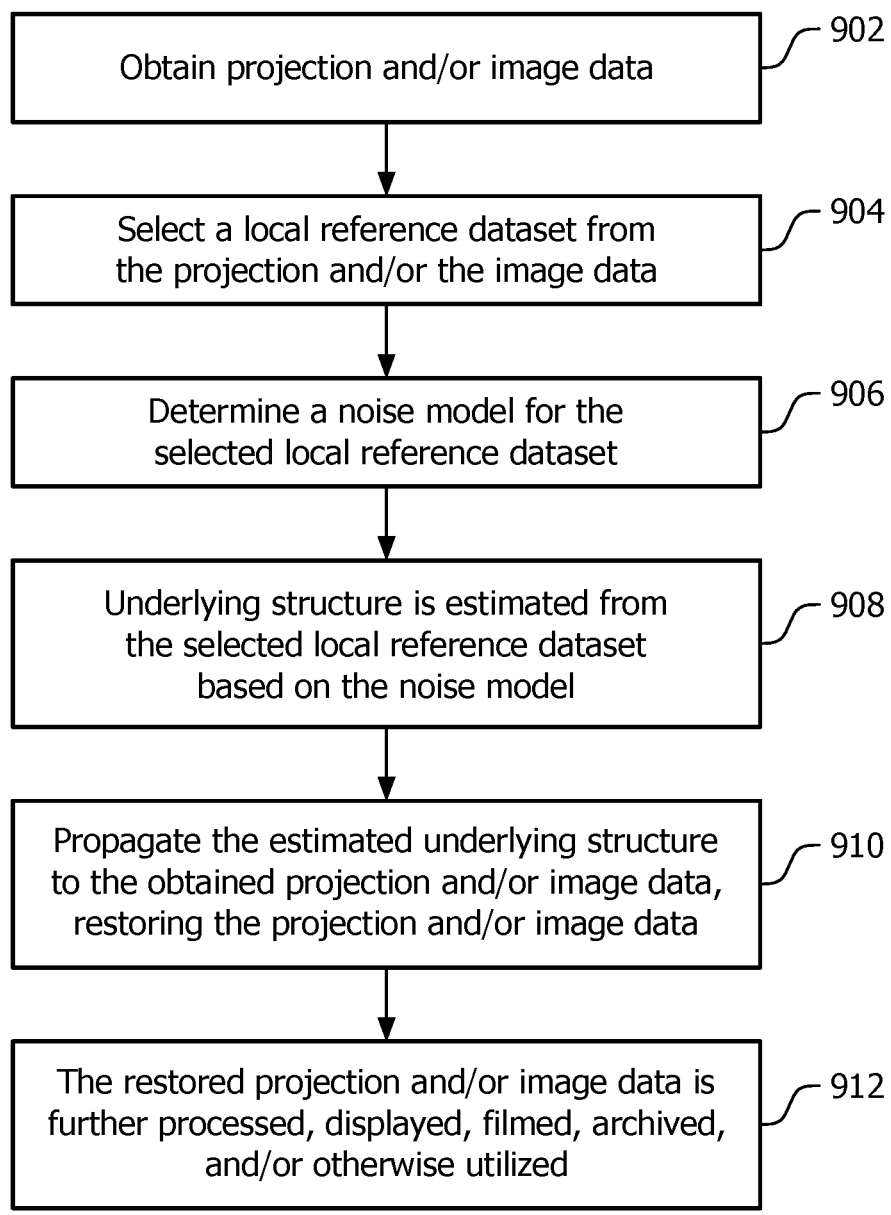
FIG. 9 illustrates an example method for processing projection data and/or image data.

FIG. 9 illustrates an example method in accordance with the disclosure herein.

It is to be appreciated that the ordering of the acts is not limiting. As such, other orderings are contemplated herein. In addition, one or more acts may be omitted and/or one or more additional acts may be included.

At 902, input projection data and/or image data are obtained.

At 904, a local reference dataset is selected from the projection data and/or the image data.

At 906, a noise model for the selected reference dataset is determined.

At 908, underlying local structure from the reference dataset is estimated based on the noise model.

At 910, the estimated structure is propagated to the projection data and/or image data, restoring the projection data and/or image data.

At 912, the restored projection data and/or the restore image data can be further processed, displayed via a display monitor, filmed, archived in a data repository, and/or otherwise utilized.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
    obtaining at least one of projection data from a spectral scan or image data generated from the projection data, wherein the at least one of the projection data or the image data is produce by a computed tomography scanner;
    selecting a local reference dataset from the at least one of the projection data or the image data;
    determining a noise pattern for the selected reference dataset;
    estimating underlying local structure from the local reference dataset based on the noise pattern by extracting a first sub-volume of voxels around a voxel in the local reference dataset, calculating a first local kernel based on the extracted first sub-volume, multiplying the first local kernel by a first spatial kernel to produce a first weight, normalizing the first weight to a sum equal to one, and estimating the underlying local structure based on the extracted first sub-volume and the normalized first weight;
    restoring at least one of the projection data or the image data by extracting a second sub-volume of voxels around a voxel in the at least one of the projection data or image data, calculating a second local kernel based on the estimated underlying local structure, multiplying the second local kernel by a second spatial kernel to produce a second weight, normalizing the second weight to a sum equal to one, and propagating the underlying local structure to the at least one of the projection data or the image data based on the extracted second sub-volume and the normalized second weight; and
    displaying the restored at least one of the projection data or the image data.

2. The method of claim 1, further comprising:
    utilizing the estimated underlying local structure as constraints on the restoration.

3. The method of claim 1, further comprising:
    adding a sub-portion of at least one of removed texture or noise back to the restored projection data or image data.

4. The method of claim 1, wherein the local reference dataset is selected from only the projection data.

5. The method of claim 1, wherein the local reference dataset is selected from only the image data.

6. The method of claim 1, wherein the local reference dataset is selected from the projection data and the projection data is restored, and further comprising:

selecting a second local reference dataset from the restored projection data;

determining a second noise pattern for the second selected reference dataset;

estimating a second underlying local structure from the second reference dataset based on the second noise pattern; and restoring the image data based on the estimated second underlying local structure.

7. The method of claim 1, wherein the local reference dataset includes one of a specific monochromatic image, a non-spectral image, a combined spectral/non-spectral image, a low energy image or a high energy image.

8. The method of claim 1, wherein the local reference dataset includes one of a specific monochromatic sinogram, a non-spectral sinogram, a combined sinogram/non-spectral sinogram, a low energy sinogram or a high energy sinogram.

9. The method of claim 1, further comprising:

selecting the local reference dataset based on a global approach in which a single reference dataset is selected for the entire at least one of the projection image or image data.

10. The method of claim 9, wherein the selection is based on one or more of: a minimum total variation; a minimum entropy; a minimum median over a local standard deviation; a minimum average of local noise estimate; and a contrast to noise ratio image based on input of two regions of interest.

11. The method of claim 1, further comprising:

selecting the local reference dataset based on a local approach in which, for each pixel, an optimal reference dataset patch is selected.

12. The method of claim 1, wherein the noise pattern is based on one or more of a Monte Carlo estimate, analytics, or direct extraction.

13. The method of claim 1, further comprising:

calculating a final restoration value for the voxel in the at least one of the projection data or image data:
$V^{Final} = \hat{V}^{Iter=N}\delta + (\hat{V}^{Iter=0} - \hat{V}^{Iter=N})(1-\delta)$, where V is a voxel, $\hat{V}_{i,j,k}^{Iter=0} = V_{i,j,k}$ is the input target dataset, Iter is an index of a current iteration, and $\delta$ is an input parameter.

14. The method of claim 1, further comprising:

calculating a final restoration value for the voxel in the at least one of the projection data or image data:
$V^{Final} = \hat{V}^{Iter=N}\delta + (R - \hat{R}^{NR})(1-\delta)$, where V is a voxel R is a pixel in the reference image dataset, Iter is an index of a current iteration, and $\delta$ is an input parameter.

15. A projection data and/or image data processor, comprising:

a memory that is configured to store a structure propagation algorithm; and a microprocessor that executes the structure propagation algorithm in connection with at least one of projection data or image data from a spectral scan to remove at least one of noise or artifacts from the at least one of projection data or the image data, while preserving underlying object structure and spectral information, wherein the microprocessor:

selects a local reference dataset from the at least one of the projection data or the image data, estimates the underlying local structure from the local reference dataset based on the noise pattern by extracting a first sub-volume of voxels around a voxel in the local reference dataset, calculating a first local kernel based on the extracted first sub-volume, multiplying the first local kernel by a first spatial kernel to produce a first weight, normalizing the first weight to a sum equal to one, and estimating the underlying local structure based on the extracted first sub-volume and the normalized first weight, and restores at least one of the projection data or the image data by extracting a second sub-volume of voxels around a voxel in the at least one of the projection data or image data, calculating a second local kernel based on the estimated underlying local structure, multiplying the second local kernel by a second spatial kernel to produce a second weight, normalizing the second weight to a sum equal to one, and propagating the underlying local structure to the at least one of the projection data or the image data based on the extracted second sub-volume and the normalized second weight.

16. The projection data and/or image data processor of claim 15, wherein the microprocessor calculates a final restoration value for the voxel in the at least one of the projection data or image data:
$V^{Final} = \hat{V}^{Iter=N}\delta + (\hat{V}^{Iter=0} - \hat{V}^{Iter=N})(1-\delta)$, where V is a voxel, $\hat{V}_{i,j,k}^{Iter=0} = V_{i,j,k}$ is the input target dataset, Iter is an index of a current iteration, and $\delta$ is an input parameter.

17. The projection data and/or image data processor of claim 15, wherein the microprocessor calculates a final restoration value for the voxel in the at least one of the projection data or image data:
$V^{Final} = \hat{V}^{Iter=N}\delta + (R - \hat{R}^{NR})(1-\delta)$, where V is a voxel, R is a pixel in the reference image dataset, Iter is an index of a current iteration, and $\delta$ is an input parameter.

18. The projection data and/or image data processor of claim 15, wherein the microprocessor restores the at least one of the projection data or image data includes, for one or more iterations of each voxel, by extracting a sub-volume of voxels around the voxel, calculating a local kernel, multiplying the local kernel by a spatial kernel, normalizing the product to have sum equal to one; and restoring each voxel.

19. The projection data and/or image data processor of claim 15, wherein the restored at least one of the projection or image data is further processed, displayed, filmed, or archived.

20. A non-transitory computer readable storage medium encoded with computer readable instructions, which, when executed by a processor, is configured to cause the processor to:

obtain at least one of projection data from a spectral scan or image data generated based on the projection data;

select a local reference dataset from the at least one of the projection data or the image data;

determine a noise pattern for the selected reference dataset;

estimate underlying local structure from the local reference dataset based on the noise pattern; and restore at least one of projection data or image data extracting a sub-volume of voxels around a voxel in the at least one of the projection data or image data, calculating a local kernel based on the estimated underlying local structure, multiplying the local kernel by a spatial kernel to produce a weight, normalizing the weight to a sum equal to one, and propagating the underlying local structure to the at least one of the projection data or the image data based on the extracted sub-volume and the normalized weight.

* * * * *